(12) United States Patent
Broderick et al.

(10) Patent No.: US 12,385,075 B2
(45) Date of Patent: Aug. 12, 2025

(54) **METHOD FOR INCREASING THE PRODUCTION OF SMALL MOLECULES IN SUBMERGED *CORYNEBACTERIUM* CULTURE**

(71) Applicant: DANISCO US INC., Palo Alto, CA (US)

(72) Inventors: Lynn Goodfellow Broderick, North East, MD (US); Perry G. Caimi, Kennett Square, PA (US); Tanja Maria Gruber, Palo Alto, CA (US); Brian G. Lefebvre, Wilmington, DE (US); Yixin Ren, West Chester, PA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 17/836,566

(22) Filed: Jun. 9, 2022

(65) Prior Publication Data

US 2022/0298534 A1 Sep. 22, 2022

Related U.S. Application Data

(63) Continuation of application No. 16/956,290, filed as application No. PCT/US2018/061914 on Nov. 20, 2018, now abandoned.

(60) Provisional application No. 62/609,976, filed on Dec. 22, 2017.

(51) Int. Cl.
*C12P 13/08* (2006.01)
*C12N 1/14* (2006.01)
*C12N 1/20* (2006.01)
*C12P 13/14* (2006.01)
*C12R 1/15* (2006.01)
*C12R 1/885* (2006.01)

(52) U.S. Cl.
CPC .............. *C12P 13/08* (2013.01); *C12N 1/145* (2021.05); *C12N 1/205* (2021.05); *C12P 13/14* (2013.01); *C12R 2001/15* (2021.05); *C12R 2001/885* (2021.05)

(58) Field of Classification Search
None
See application file for complete search history.

(56) References Cited

U.S. PATENT DOCUMENTS 6,830,903 B1 * 12/2004 O'Donohue ............ C12P 13/06
435/106

FOREIGN PATENT DOCUMENTS

| EP | 0469517 A2 | 2/1992 | |
|---|---|---|---|
| WO | 2005/001036 A2 | 1/2005 | |
| WO | WO-2010096673 A1 * | 8/2010 | ............. C12N 1/005 |
| WO | 2014/200657 A1 | 12/2014 | |

OTHER PUBLICATIONS

Lubitz et al., Ciprofloxacin triggered glutamate production by Corynebacterium glutamicum, BMC Microbiol. 16, 2016, 235. (Year: 2016).*
Abo-State et al., Bioethanol Production from Rice Straw Enzymatically Saccharified by Fungal Isolates, Trichoderma viride F94 and Aspergillus terreus F98, Soft 3, 2014, 19-29. (Year: 2014).*
Cao et al., Improving the stability of glutamate fermentation by Corynebacterium glutamicum via supplementing sorbitol or glycerol, Bioresources Bioprocessing 2, 2015, 9. (Year: 2015).*
Jorgensen et al., Enzyme recycling in lignocellulosic biorefineries, Biofuels, Bioproducts & Biorefining 11, 2017, 150-67. (Year: 2017).*
Shibata et al., A novel GH10 xylanase from *Penicillium* sp. accelerates saccharification of alkaline-pretreated bagasse by an enzyme from recombinant Trichoderma reesei expressing Aspergillus β-glucosidase, Biotechnol. Biofuels, Nov. 10, 2017, 278. (Year: 2017).*
Enzyme, Dictionary of Microbiol. & Mol. Biol., 2016, https://search.credoreference.com/articles/Qm9va0FydGljbGU6OTYzNDI1?q=Enzyme&aid=279753. (Year: 2016).*
Cao et al., Improving the stability of glutamate fermentation by Corynebacterium glutamicum via supplementing sorbitol or glycerol, Bioresources Bioeng. 2, 2015, 9. (Year: 2015).*
Ahmed, Aftab et al., Effect of culture medium composition on Trichoderma reesei's morphology and cellulase production, Bioresource Technology, Dec. 2009, pp. 5979-5987, vol. 100, Issue 23.
De Graaf, A.A., et al., Metabolic Engineering for L-Lysine Production by Corynebacterium glutamicum, Advances in Biochemical Engineering/Biotechnology, 2001, pp. 9-29.
Hermann, Thomas, Industrial production of amino acids by coryneform bacteria, J. Biotechnology, 2003, vol. 104, pp. 155-172.
Keränan, Sirkka et al., Production of recombinant proteins in the filamentous fungus *Trichoderma reesei*, Current Opinion in Biotechnology, 1995, pp. 534-537, vol. 6.
Kusumoto, Isao, Industrial Production of L-Glutamine1, Journal of Nutrition, 2001, pp. 2552S-558, vol. 131, Issue 9.
Luo, Zhiting et al., Microbial synthesis of poly-γ-glutamic acid: current progress, challenges, and future Perspectives, Biotechnology for Biofuels, 2016, vol. 9:134, 12 pages.
Nevalainen, Helena et al., Making recombinant proteins in filamentous fungi—are we expecting too much?, Frontiers in Microbiology, Feb. 27, 2014, vol. 5, Article 75, 10 pages.
Wendisch, Volker F. et al., Updates on industrial production of amino acids using Corynebacterium glutamicum, World Journal of Microbiology and Biotechnology, 2016, vol. 32, Article No. 105.
Zahoora, Ahmed et al., Metabolic Engineering of Corynebacterium Glutamicum Aimed At Alternative Carbon Sources and New Products, Computational and Structural Biotechnology Journal, Oct. 2012, vol. 3, Issue 4, e201210004.
International Search Report and Written Opinion—PCT/US2018/061914—mailed Feb. 13, 2019.

* cited by examiner

*Primary Examiner* — Todd M Epstein

(57) ABSTRACT

Described are methods for increasing the production of small molecules in a submerged *Corynebacterium* culture by supplementing *Corynebacterium* growth medium with the non-enzymatic fraction of spent *Trichoderma* fermentation broth.

7 Claims, 2 Drawing Sheets

METHOD FOR INCREASING THE PRODUCTION OF SMALL MOLECULES IN SUBMERGED *CORYNEBACTERIUM* CULTURE

CROSS REFERENCE

This application is a Continuation of U.S. application Ser. No. 16/956,290, filed Jun. 19, 2020, which is a 371 of International Application No. PCT/US18/61914, filed Nov. 20, 2018, which claims the benefit of U.S. Provisional Application No. 62/609,976, filed Dec. 22, 2017, all of which are incorporated by reference in their entirety.

BACKGROUND

*Corynebacterium* are gram-positive, aerobic bacilli that include members useful for industrial applications as well as human pathogens. Nonpathogenic species of *Corynebacterium* are used for the production of amino acids, nucleotides, steroids, bacteriocins, and enzymes. The most well-known species is *C. glutamicum*, which produces glutamic acid sold as monosodium glutamate in the food industry. Genetically engineered *C. glutamicum* produce lysine. *Corynebacterium* are generally grown in submerged culture using glucose, fructose, or glucose plus fructose and sucrose as a primary carbon source.

*Trichoderma* is a genus of filamentous fungi that is present in soil. Many species are characterized as opportunistic, avirulent plant symbionts. *Trichoderma* produce a wide array of enzymes, including cellulases and hemicellulases. *Trichoderma* has also been engineered to produce and secrete recombinant enzymes, such as catalase, glucoamylase, laccase and the like. The productivity of *Trichoderma* is very high, and titers of over 100 grams of recombinant enzyme per liter of submerged culture are not uncommon. Some *Trichoderma* enzyme products are sold as whole broth products, usually including killed cells. Other *Trichoderma* enzyme products are sold in purified form, in which case spent *Trichoderma* growth media is discarded.

SUMMARY

The present methods relate to increasing the production of small molecules in a submerged *Corynebacterium* culture by supplementing *Corynebacterium* growth medium with the non-enzymatic fraction of spent *Trichoderma* fermentation broth. Aspects and embodiments of the methods are described in the following, independently-numbered paragraphs.

1. In one aspect, a method for improving the production of small molecules in submerged *Corynebacterium* culture is provided, comprising adding to a submerged *Corynebacterium* culture a non-enzymatic fraction of spent *Trichoderma* fermentation broth, wherein the *Corynebacterium* grown in the presence of the non-enzymatic fraction of spent *Trichoderma* fermentation broth produce an increased amount of small molecules compared to *Corynebacterium* grown in an otherwise identical submerged culture in the absence of the non-enzymatic fraction of spent *Trichoderma* fermentation broth, wherein the increase in small molecule production is not due to enzymatic activity in the spent *Trichoderma* fermentation broth.

2. In some embodiments of the method of paragraph 1, the non-enzymatic fraction of spent *Trichoderma* fermentation broth is produced by filtering whole or fractionated spent *Trichoderma* fermentation broth.

3. In some embodiments of the method of paragraph 1, the non-enzymatic fraction of spent *Trichoderma* fermentation broth is produced by heat treating whole or fractionated spent *Trichoderma* fermentation broth.

4. In some embodiments of the method of paragraph 1, the non-enzymatic fraction of spent *Trichoderma* fermentation broth used to increase small molecule production is a component of whole or fractionated spent *Trichoderma* fermentation broth that is added to the submerged *Corynebacterium* culture.

5. In some embodiments of the method of any of the preceding paragraphs, the non-enzymatic fraction of spent *Trichoderma* fermentation broth is a by-product of a fermentation that produces a recombinant enzyme.

6. In some embodiments of the method of paragraph 5, the non-enzymatic fraction of *Trichoderma* fermentation broth used to increase small molecule production additionally comprises the recombinant enzyme.

7. In some embodiments of the method of paragraph 5, the recombinant enzyme is removed from the non-enzymatic fraction of *Trichoderma* fermentation broth used to improve small molecule production.

8. In some embodiments of the method of any of paragraphs 5-7, the recombinant enzyme is a carbohydrate processing enzyme.

9. In some embodiments of the method of any of the preceding paragraphs, at least a portion of the spent fermentation broth is added at the time of inoculation of the *Corynebacterium* culture.

10. In some embodiments of the method of any of the preceding paragraphs, the spent fermentation broth is harvested from a *Trichoderma* growth culture at least 29 hours following inoculation of *Trichoderma* broth.

11. In some embodiments of the method of any of the preceding paragraphs, the spent fermentation broth is harvested from a *Trichoderma* growth culture prior to the expression of a protein of interest in the broth.

12. In some embodiments of the method of any of the preceding paragraphs, the small molecule is an amino acid.

13. In some embodiments of the method of paragraph 12, the amino acid is glutamic acid or lysine.

14. In some embodiments of the method of any of the preceding paragraphs, the increase in small molecule production is not the result of increased cell mass in the *Corynebacterium* culture.

15. In another aspect, a small molecule produced in submerged *Corynebacterium* culture produced by the method of any of paragraphs 1-14 is provided.

16. In another aspect, use of a non-enzymatic fraction of spent *Trichoderma* fermentation broth to increase the amount of small molecules produced in a submerged *Corynebacterium* culture is provided.

17. In some embodiments, use of a non-enzymatic fraction of spent *Trichoderma* fermentation broth as in paragraph 16 is combined with the features of any of paragraphs 1-14.

These and other aspects and embodiments of present methods will be apparent from the description, including the accompanying Figures.

DETAILED DESCRIPTION

I. Introduction

Figure 1:
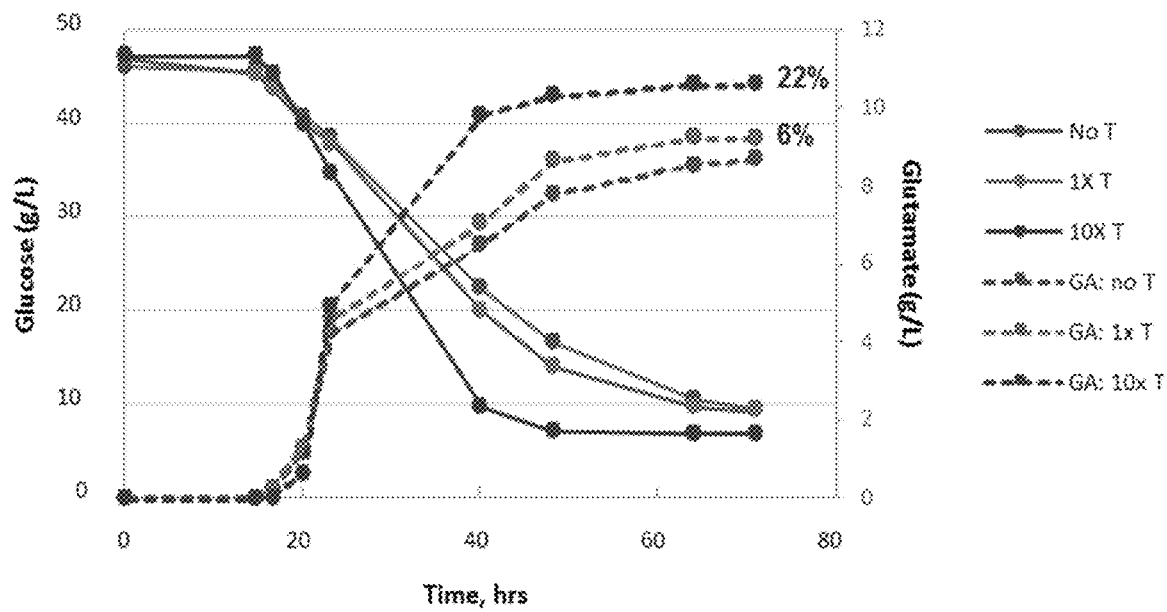
FIG. 1 is a graph showing glucose consumption (g/L) and glutamate production (g/L) over time (hrs) in a *Corynebacterium* culture to which spent *Trichoderma* fermentation broth has been added.

The present methods relate to increasing the production of small molecules in a submerged *Corynebacterium* culture by supplementing *Corynebacterium* growth medium with the non-enzymatic fraction of spent *Trichoderma* fermentation broth.

II. Definitions and Abbreviations

Prior to describing the methods in detail, the following terms are defined for clarity. Terms not defined should be accorded their ordinary meanings as used in the relevant art.

As used herein, "submerged culture" refers to a method for growing cultures of microorganisms in which the microorganisms are incubated in a liquid medium subjected to continuous, vigorous agitation.

As used herein, a "fermenting organism" is a microorganisms capable of producing a product of interest, such as an amino acid or a protein, when grown in submerged culture.

As used herein, a "spent broth" refers to submerged culture growth medium in which a microorganism has been grown. Spent broth contains chemical compounds secreted into the medium. "Whole spent" broth additionally includes the microorganisms (cells) grown in the medium. "Fractionated spent broth" has been processed in some way so as to remove at least some of the components in the spent broth.

As used herein, a "non-enzymatic fraction" of a spent broth is either substantially free of enzymatic protein or is substantially free of enzymatic activity, even though denatured enzymatic proteins may be present.

As used herein, a "small molecule" is a low molecular weight (<900 Da) organic compound that that is not a polymer.

As used herein, "*Trichoderma*" is the genus of an organism having the following lineage as of 2017 according to the National Center for Biotechnology Information (NCBI, Bethesda MD, USA): Eukaryota; Opisthokonta; Fungi; Dikarya; Ascomycota; saccharomyceta; Pezizomycotina; leotiomyceta; sordariomyceta; Sordariomycetes; Hypocreomycetidae; Hypocreales; Hypocreaceae.

As used herein, "*Corynebacterium*" is the genus of an organism having the following lineage as of 2017 according to the NCBI: Bacteria; Terrabacteria group; Actinobacteria; Actinobacteria; Corynebacteriales; Corynebacteriaceae.

As used herein, the singular articles "a," "an," and "the" encompass the plural referents unless the context clearly dictates otherwise. All references cited herein are hereby incorporated by reference in their entirety.

The following abbreviations/acronyms have the following meanings unless otherwise specified:

Da Dalton
w/v weight/volume
w/w weight/weight
v/v volume/volume
° C. degrees Centigrade
g or gm gram
microgram
mg milligram
kg kilogram
μL and μl microliter
mL and ml milliliter
mm millimeter
micrometer
mol mole
mmol millimole
M molar
mM millimolar
micromolar
nm nanometer
ppm parts per million
hr or hrs hour
RPM revolutions per minute
SLPM standard liters per minute

III. Spent *Trichoderma* Broth

*Trichoderma* is widely used to produce and secrete recombinant enzymes on an industrial scale (see, e.g., Keränen, S. and Penttilä, M. (1995) *Current Opinion in Biotechnology* 6:534-37; Ahamed, A. and Vermette, P. (2009) *Bioresource Technology* 100:5979-87; and Helena Nevalainen, H and Petersonl, R. (2014) *Front Microbiol.* 5:75). Strains, medium components and culture conditions are well known.

The present methods relate to the use of whole or fractionated spent *Trichoderma* fermentation broth, necessarily including the non-enzymatic fraction of the spent broth, to increase the amount of small molecules produced by *Corynebacterium* grown in submerged culture.

In some embodiments, only the non-enzymatic fraction of spent *Trichoderma* broth is added to the *Corynebacterium* culture. This fraction may be substantially free of enzymes, meaning that protein having enzymatic activity are not present in the broth, or may be substantially free of active enzymes, meaning that enzymatic activity in the broth has been destroyed by physical or chemical treatment of the broth.

Enzymatic activity may be eliminated by filtration of spent *Trichoderma* broth to separate components responsible for the beneficial effect on *Corynebacterium* cultures from proteins having enzymatic activity. Such filtration may encompass filtration to remove proteins having a molecular weight of greater than about 30K Da.

Enzymatic activity may alternatively or additionally be destroyed by heating the spent *Trichoderma* broth to a temperature above about 70° C., above about 75° C., above about 80° C., above about 85° C., above about 90° C. or even above about 95° C., for a time sufficient to denature enzyme, e.g., at least about 10 min, at least about 15 min, at least about 20 min, at least about 30 min, or at least about 40 min, or more.

Enzymatic activity may alternatively or additionally be destroyed by incubating the spent *Trichoderma* broth with small molecule protease inhibitors, or other small molecules that inhibit the activity of particular classes of enzymes.

Enzymatic activity may alternatively or additionally be destroyed by incubating the spent *Trichoderma* broth with active proteases, which may be exogenous to the spent *Trichoderma* broth such that proteins present in the spent *Trichoderma* broth are digested and substantially no enzymatic activity remains in the spent *Trichoderma* broth.

Enzymatic activity may alternatively or additionally be destroyed by subjecting the spent *Trichoderma* broth to chromatography methods routinely used to separate proteins from other components in the spent *Trichoderma* broth, the separated proteins being the source of enzymatic activity in the spent *Trichoderma* broth.

Enzymatic activity may alternatively or additionally be destroyed by reducing or eliminating the expression and/or secretion of native or non-native (i.e., recombinant) proteins, which may be enzymes, by selecting a particular strain of *Trichoderma*, or genetically modifying *Trichoderma* to eliminate or reduce the expression or secretion of enzymes in the spent *Trichoderma* broth.

The non-enzymatic fraction of spent *Trichoderma* broth may be included in whole or otherwise fractionated spent *Trichoderma* broth as a specialized product. Alternatively, the non-enzymatic fraction of spent *Trichoderma* broth may be provided as a specialized, fractionated product of a spent *Trichoderma* broth.

In some embodiments, only the non-enzymatic fraction of spent *Trichoderma* broth further includes one or more proteins of interest, for example, carbohydrate-processing enzymes and other commercially-relevant polypeptides, including but not limited to a dehydrogenase, a transketolase, a phosphoketolase, a transladolase, an epimerase, a phytase, a xylanase, a β-glucanase, a phosphatase, a protease, an α-amylase, a β-amylase, a glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase.

In other embodiments, only the non-enzymatic fraction of spent *Trichoderma* broth specifically excludes any particular protein of interest, including an enzymatic protein of interest, and particularly a recombinant protein of interest.

In some embodiments, the spent *Trichoderma* broth or fraction, thereof, is formulated, e.g., for storage stability or ease of handling. Formulation components include, but are not limited to, glycerol, sorbitol, salts, polymers, preservatives and the like.

IV. Submerged *Corynebacterium* Cultures

As described, herein, the present methods involve the addition of spent *Trichoderma* broth to cultures of *Corynebacterium* that produce small molecules. *Corynebacterium* naturally produce significant amounts of glutamate and can readily be genetically modified to produce other products, including but not limited to lysine (see, e.g., de Graaf, A. A. et al. (2001) *Adv Biochem Eng Biotechnol.* 73:9-29 and Wendisch, V. F. et al. (2016) *World J Microbiol Biotechnol.* 32:105). Numerous strains of *Corynebacterium* are commercially available, the most common being derivatives of *C. glutamicum*. The complete genomic sequence of *C. glutamicum* 59114 is known.

Conditions for growing *Corynebacterium* in submerged culture for the purpose of producing commercially-valuable products are well-known, as is described in, for example, in Kusumoto, I. (2001) *J. Nutr.* 131:2552S-55S; Hermann, T. (2003) *J Biotechnol.* 104:155-172; Zhiting Luo, Z. et al. (2016) *Biotechnology for Biofuels* 9:134; and Zahoora, A. et al. (2012) *CSBJ.* 3: e201210004.

*Corynebacterium* growth medium generally includes a primary carbon source such as glucose, fructose or sucrose, although carbon sources such as cane molasses, xylose, agro-industrial wastes, rapeseed meal, soybean residue, corncob fibers and glycerol have also been used. Yeast extract is a suitable nitrogen source but ammonium sulfate and ammonium chloride are more cost effective. Inorganic salts and particularly manganese can affect the productivity of *Corynebacterium*.

In some embodiments, the amount of whole or fractionated spent *Trichoderma* broth as a percentage of the total amount of *Corynebacterium* growth medium at least 0.01%, at least 0.02%, at least 0.03%, at least 0.04%, at least 0.05%, at least 0.06%, at least 0.07%, at least 0.08%, at least 0.09%, at least 0.10%, at least 0.12%, at least 0.14%, at least 0.16%, at least 0.18%, at least 0.2%, at least 0.3%, at least 0.4%, at least 0.5%, at least 0.6%, at least 0.7%, at least 0.8%, at least 0.9%, at least 1%, at least 2%, at least 5%, or more (v/v).

Whole or fractionated spent *Trichoderma* broth is preferably added at the time of inoculation of the *Corynebacterium* culture. However, during fed-batch fermentation, it may be desirable to stagger the addition of the spent *Trichoderma* broth. For example, 50% of the dose of *Trichoderma* broth may be added at the time of inoculation of the *Corynebacterium* culture, followed by the addition of 25% at about 10 hours, and the remaining 25% at about 16 hours post inoculation.

These and other aspects and embodiments of the present methods will be apparent to the skilled person in view of the present description. The following examples are intended to further illustrate, but not limit, the methods.

EXAMPLES

Example 1. Organisms, Culture Media and Spent Broth

*Corynebacterium glutamicum* strains ATCC13032 and ATCC15990 from the American Type Culture Collection (Manassas, VA, USA) were used for all L-glutamate experiments.

*Corynebacterium glutamicum* strain ATCC 21513, from the American Type Culture Collection (Manassas, VA, USA) was used for all L-Lysine production experiments.

*Trichoderma reesei* strain Morph, described in PCT App. No. WO 05/001036, was used for all experiments.

*Trichoderma reesei* whole spent broth contained (w/w) water (80-98%), and (%) at a pH of 4.5-5.0.

Formulated *Trichoderma reesei* whole spent broth contained (w/w) water (33-45%), glycerol (47-53%) and sodium chloride (3-4%) at a pH of 4.5-5.0.

CGXII media contained (per liter) 50 g glucose, 20 g ammonium sulfate, 5 g urea, 1 g potassium phosphate (monobasic), 1 g potassium phosphate (dibasic), 0.25 g magnesium sulfate, 42 g 3-(N-morpholino)propanesulfonic acid (MOPS), 10 μg calcium chloride, 35 μg 3,4-dihydroxybenzoic acid, trace elements (1 mg $FeSO_4$, 1 mg $MnSO_4$, 0.1 mg $ZnSO_4$, 0.02 mg $CuSO_4$ and 0.002 mg $NiCl_2$), 1.0 μg biotin adjusted to pH 7.0 using sodium hydroxide.

Glutamic acid batch fed fermentation medium contained (per liter) 15 g Sigma corn steep solids, 10 g $(NH_4)_2PO_4$, 2.0 g $K_2HPO_4$, 0.5 ml Sigma 204 antifoam, 50 mL 100× trace elements solution (containing 80 g $MGSO_4·7H_2O$, 2.2 g $FeSO_4·7H_2O$, and 2.2 g $MnSO_4·H_2O$) and 5 mL of 1000× vitamin solution (containing 0.2 g vitamin B1 thiamine), 545 g of 55% w/w glucose.

Lysine seed flask medium contained per liter 5.0 g Difco yeast extract, 10 g Difco select soytone, 10 g NaCl and 10.0 g glucose.

Lysine fermentation medium contained per liter 52.5 g soy meal hydrolysate, 2.4 g molasses, 12.4 g $(NH_4)_2SO_4$, 0.7 g citric acid monohydrate, 2.2 g 85% H₃PO₄, 1.24 g MgSO₄·7H₂O, 1.24 g MnSO₄·H₂O, 0.002 g ZnSO₄·7H₂O, 0.038 g FeSO₄·7H₂O, 0.55 g L-threonine, 0.60 g L-methionine, 0.0006 g biotin, 0.00024 g thiamine hydrochloride, 0.5 ml Sigma 204 antifoam, batch in initial bolus of 545 g of 55% w/w 95DE (Cargill 95DE dextrose.

Lysine carbon source feed contained: 55% w/w 95DE (Cargill 95DE dextrose)

Example 2. Stimulation of Glutamate Production by *Corynebacterium*

Formulated *Trichoderma reesei* whole spent broth was added to shake-flask assays containing one of two different *C. glutamicum* strains to determine the effect on glutamic acid titer and reduce fermentation time. *C. glutamicum* strains ATCC13032 and ATCC15990 were grown from glycerol stocks on LB agar plates by incubating at 30° C. Cells were transferred to liquid CGXII media and incubated overnight at 30° C. with shaking (250 RPM). Cells were transferred a second time and grown overnight in CGXII media before using in production flasks.

The ATCC13032 *Corynebacterium* cells were then inoculated into fresh CGXII media at an initial OD of 0.025-0.1 (600 nm) and spent *Trichoderma* broth was added (or water as a negative control) at different concentrations/dosages. A 1× dosage represents a 1250-fold dilution of spent *Trichoderma* broth in *Corynebacterium* medium (0.08% of the total volume). A 5× dosage represents a 625-fold dilution (i.e., 0.4% of the total volume) and a 10× dosage represents a 125-fold dilution (0.8% the total volume).

Flasks were incubated at 30° C. with shaking (250 RPM) for about 48 hr. At the end of this incubation, the final cell mass was determined using the absorbance at 600 nm and the glutamic acid concentration was determined using HPLC analysis (pre-column derivatization with o-phthalaldehyde, C18 column and a methanol/acetonitrile gradient as the mobile phase). Each concentration was tested in duplicate with the average results shown in Table 1.

TABLE 1

Effect of spent *Trichoderma* broth on ATCC13032 cell mass and glutamate production

|  | Control | 1X | 5X | 10X |
|---|---|---|---|---|
| OD (A 600 nm) | 16.85 | 18.20 | 22.65 | 25.80 |
| % increase vs. control | — | 7% | 26% | 35% |
| Glutamic acid (g/L) | 5.77 | 6.73 | 10.02 | 10.18 |
| % increase vs. control | — | 14% | 42% | 43% |

The results show a dose dependent response increase in cell mass and glutamic acid production in the presence of spent *Trichoderma* broth up to a saturation point where no further increase possible, likely due to complete conversion of available sugar.

The experiment was repeated using the ATCC15990 strain using a 10× dose (0.8% volume) of spent *Trichoderma* broth in the *Corynebacterium* CGXII media. The results are shown in Table 2.

TABLE 2

Effect of spent *Trichoderma* broth on ATCC15990 cell mass and glutamate production

|  | Control | 10X |
|---|---|---|
| OD (A 600 nm) | 15.6 | 25.45 |
| % increase vs. control | — | 39% |
| Glutamic acid (g/L) | 6.83 | 10.1 |
| % increase vs. control | — | 32% |

Additional spent *Trichoderma* broth samples were tested in duplicate to determine if the positive effect on glutamic acid production was an isolated phenomenon. A total of five spent *Trichoderma* whole broths (A-E) were tested as described, above, at a 10× dose, using the ATCC13032 strain. The results show a consistent increase in glutamic acid production in the presence of any of the tested spent *Trichoderma* broths (Table 3).

TABLE 3

Effect of different spent *Trichoderma* broths on cell mass and glutamate production

|  | Control | A | B | C | D | E |
|---|---|---|---|---|---|---|
| OD (A600 nm) | 15.2 | 19.2 | 17.3 | 17.0 | 17.4 | 27.6 |
| % increase vs. control | — | 21% | 12% | 11% | 13% | 45% |
| Glutamic acid (g/L) | 5.6 | 6.6 | 7.1 | 7.0 | 7.4 | 11.0 |
| % increase vs. control | — | 16% | 21% | 21% | 25% | 50% |

The effect of media and formulation components associated with the spent *Trichoderma* broth was ruled out by adding fresh (i.e., non-inoculated) *Trichoderma* medium, citric acid or glycerol to *Corynebacterium* cultures in the same manner in which spent *Trichoderma* broth was added. No increase in cell mass or glutamic acid was detected (data not shown).

Example 3. Time-Course *Corynebacterium* Culture Experiment

Analysis of glucose consumption and glutamic acid production over time was performed in a similar shake-flask assay using 1× and 10× doses of formulated spent *Trichoderma* broth. Samples of the *Corynebacterium* cultures (ATCC13032 strain) were taken periodically over a period of about 70 hr. The results are shown in FIG. 1. The results show that the addition of spent *Trichoderma* broth produces an increase in glutamic acid production that persists throughout the time-course.

Example 4. Treatment of Spent *Trichoderma* Broth to Abolish Enzymatic Activity

Spent *Trichoderma* broth contains numerous enzymes which could affect the growth of *Corynebacterium*. To test whether any of these enzyme could be responsible for effects observed in the previous Examples, spent *Trichoderma* broth was treated to inactivate the enzymes. Specifically, spent *Trichoderma* broth was centrifuged at 14K×g for 20 minutes and the supernatant collected. The supernatant was filtered through a 30 kDa membrane (labeled, "<30K") and the permeate collected for testing in *Corynebacterium* cultures. A portion of the filtered sample was further heat treated at 90° C. for 30 minutes (labeled, "Heat"). The treated samples were found to contain much lower levels of total protein compared to the crude spent *Trichoderma* broth when visualized by SDS-PAGE analysis. The activity of an enzyme known to be over-expressed in the crude spent *Trichoderma* broth was assayed for in the treated spent *Trichoderma* broth, and no activity was detected (data not shown).

TABLE 4

Effect of treated spent *Trichoderma* broth on cell mass and glutamate production

|  | Control | 10X | 10X < 30 kD | 10X Heat |
|---|---|---|---|---|
| OD (A 600 nm) | 18.5 | 29.9 | 30.2 | 29.3 |
| % increase vs. control | — | 38% | 39% | 37% |
| Glutamic acid (g/L) | 5.7 | 10.6 | 10.5 | 10.8 |
| % increase vs. control | — | 46% | 46% | 47% |

Despite the lack of enzyme activity and near-complete absence of protein, the treated spent *Trichoderma* broth still improved glutamic acid production at a 10× dosage, as demonstrated by shake-flask assay summarized in Table 4.

Example 5. Time-Course *Trichoderma* Culture Experiment

Figure 2:
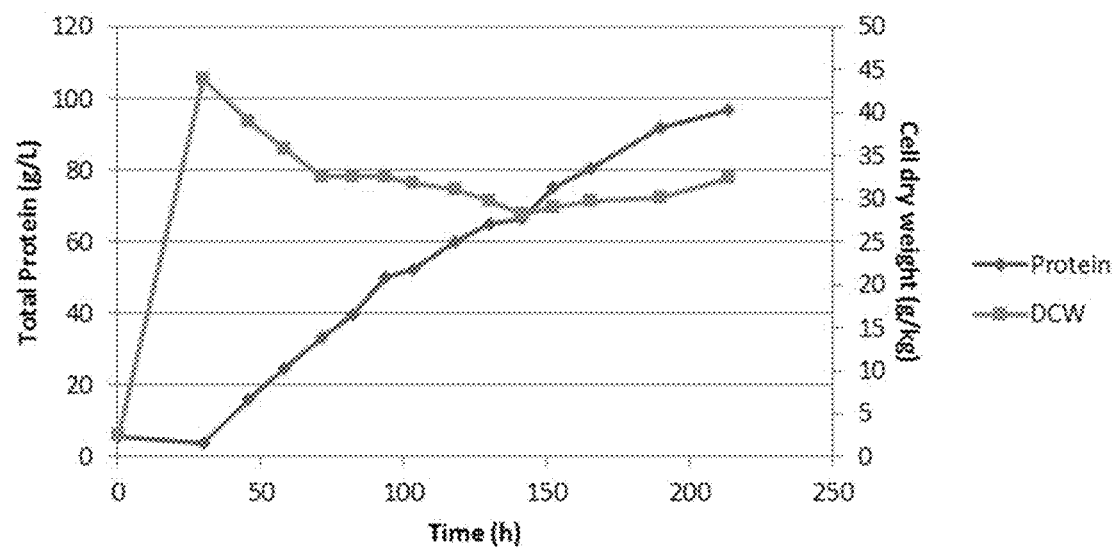
FIG. 2 is a graph showing total secreted protein production (g/L) and dry cell weight (g/kg) in a *Trichoderma* culture from which spent *Trichoderma* fermentation broth was periodically sampled.

To determine when the non-enzymatic components that increase production of glutamate by *Corynebacterium* appear in the spent *Trichoderma* broth, a time-course experiment involving a *Trichoderma* culture was performed. *Trichoderma* was grown in culture for up to 213 hr and samples of spent broth were taken periodically. The dry cell weight ("DCW") and levels of secreted protein in the culture are shown in FIG. 2. Each time-point sample was filtered through a 0.2 µM filter to remove cells.

Figure 3:
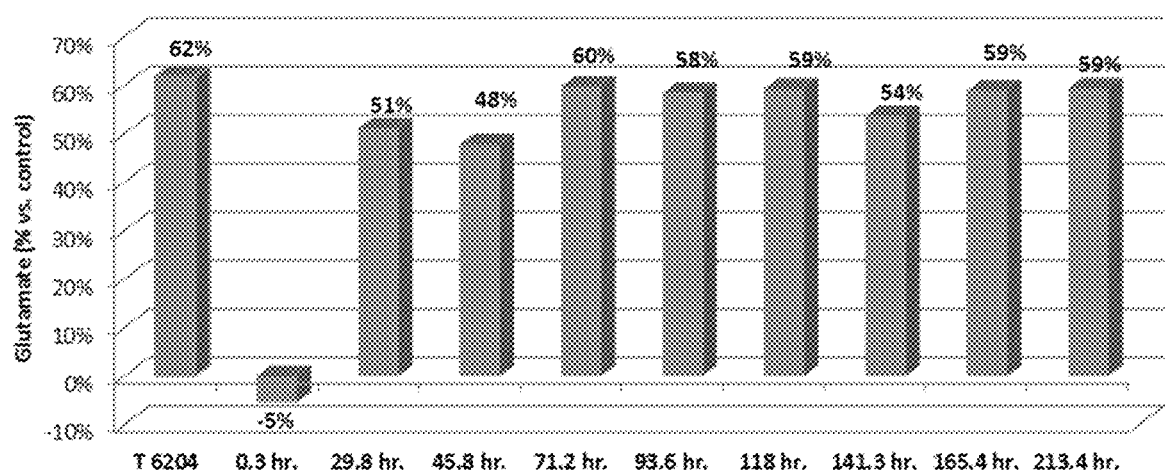
FIG. 3 is a graph showing the effect of spent *Trichoderma* fermentation broth taken from a *Trichoderma* culture as different time points (hrs) on glutamate production (g/L) in a *Corynebacterium* culture.

Samples of spent *Trichoderma* broth taken at the different time points was then added to *Corynebacterium* shake flask cultures at a 10× dosage and the amount of glutamate produced was measured as described, above. The results are shown in FIG. 3. The results show that the non-enzymatic component present in spent *Trichoderma* broth that improves glutamate production by *Corynebacterium* is not present at the 0.3-hour time-point during the growth of the *Trichoderma* culture. However, the component is present very early in the fermentation time, at least by 29 hours, and remains during the entire fermentation. Notably, the secreted protein levels are very low at the 29-hour time point. This particular *Trichoderma* organism also over-expressed a different protein compared to the one used in the previous Examples, further emphasizing that the observed effect on *Corynebacterium* cultures is not dependent on the gene of interest that *Trichoderma* may express.

Example 6. Stimulation of Glutamic Acid Production in Fed-Batch Fermentation

Formulated *T. reesei* whole spent broth or processed broth was added to fermentors containing *C. glutamicum* to determine the effect on glutamic acid production rate, titer, and yield. *C. glutamicum* strain ATCC 13032 was grown from glycerol stocks in glutamic acid seed flask medium and incubated overnight at 30° C. with shaking (200 RPM). Cells were transferred to seed flasks and grown overnight in the same medium before using in production fermentors. The overnight seed cultures were used to inoculate glutamic acid fermentation media at an initial OD of 0.1 (600 nm). Fermentations were performed at 30° C. with mixing to maintain a dissolved oxygen of 30% controlled by stirring with a minimum set point 300 rpm to maximum of 1200 rpm, followed by over-pressurization to a maximum of 1.5 bar and aeration to a maximum 10.0 (standard liter per minute) for the duration of the fermentation run.

A carbon source feed, containing 55% w/w 95DE (Cargill 95DE dextrose), having a constant feed rate of 0.75 g/min, was used beginning at 14 hours elapsed fermentation time. A 1× or 5× dose of whole spent *Trichoderma* broth or a 1× dose of heat-treated spent broth (or no broth as a control) was added to the *Corynebacterium* fermentations. One-half of the total dose of *Trichoderma* broth was added at the time of inoculation with *Corynebacterium*, 25% at 10 hours, and the remaining 25% at 16 hours post inoculation.

At the end of this incubation, the final glutamic acid concentration was determined using HPLC analysis (pre-column derivatization with o-phthalaldehyde, C18 column and a methanol/acetonitrile gradient as the mobile phase) using a 1200 Series Agilent Technologies Fluorescence detector. The results in Table X summarize the results in terms of percent increase in the rate, titer, and yield of glutamic acid at the end of fermentation, compared to the untreated control tank. The results show titer of glutamic acid (reported as acid) in the control fermentor was lower, compared to the test tanks. Fermentors containing either a 1× or 5× dose of whole spent *Trichoderma* broth or 1× dose heat-treated whole spent *Trichoderma* broth higher levels of glutamic acid than the control. The results also show an increased rate and yield of glutamic acid at end of fermentation, compared to the untreated control tank.

TABLE 5

Effect of treated spent *Trichoderma* broth on glutamic acid production in fed-batch fermentation

| Fermentation Parameters | Glutamate titer | Glutamate volumetric rate | Glutamate yield |
|---|---|---|---|
| Control | 0.0 | 0.0 | 0.0 |
| 1X dose | 9.5 | 8.6 | 5.2 |
| 1X heat-treated dose | 4.6 | 4.5 | 5.9 |
| 5X dose | 12.9 | 11.9 | 6.8 |

Example 7. Stimulation of Lysine Production by *Corynebacterium*

Formulated *Trichoderma* whole spent broth or heat-treated broth was added to fermentors containing *C. glutamicum* strain ATCC 21513 to determine the effect on L-Lysine titer and reduced fermentation time. *C. glutamicum* strain ATCC 21513 was grown from glycerol stock media and incubated overnight at 30° C. with shaking (250 RPM) in lysine seed medium. Cells were transferred to larger seed flasks and grown overnight in liquid seed flask media before using in production fermentors. The cells were then inoculated into fresh lysine fermentation media at an initial OD of 0.1 (600 nm) and spent *Trichoderma* broth or processed broth was added at different concentrations/dosages. A 1× dosage represents 0.10% weight of fermentation medium.

Fermentations were performed at 30° C. with mixing to maintain a dissolved oxygen of 30% controlled by stirring at a maximum of 1200 rpm, followed by over-pressurization to a maximum of 1.5 bar and aeration to a maximum 10.00 SLPM for the duration of the fermentation run. A lysine carbon source feed, containing 55% w/w 95DE (Cargill 95DE dextrose), having a constant feed rate of 0.75 g/min, was used beginning at 14 hours elapsed fermentation time 14. A 1× or 5× dose of whole spent *Trichoderma* broth or a 1× dose of heat-treated spent broth (or no broth as a control) was added to the *Corynebacterium* fermentations. One-half of the total dose of *Trichoderma* broth was added at the time of inoculation with *Corynebacterium*, 25% at 10 hours, and the remaining 25% at 16 hours post inoculation.

At the end of this incubation, the final L-Lysine concentration was determined using HPLC analysis (pre-column derivatization with o-phthalaldehyde, C18 column and a methanol/acetonitrile gradient as the mobile phase) using a 1200 Series Agilent Technologies Fluorescence detector.

The results in Table 6 further summarize the results in terms of percent increases in the rate, titer, and yield of lysine at the fermentation at end of the run compared to the control. Peak lysine titers were observed at the end of the run. The results show a significant increase in lysine yield in the presence of spent *Trichoderma* broth.

TABLE 6

Effect of treated spent *Trichoderma* broth on lysine production

| Spent broth | Increase in lysine titer | Increase in lysine volumetric rate | Increase in lysine yield |
| --- | --- | --- | --- |
| None | 0 | 0 | 0 |
| 1X whole | 7.79 | 7.82 | 6.96 |
| 1X heated | 17.47 | 17.00 | 18.27 |
| 5X whole | 20.50 | 19.98 | 17.49 |

What is claimed is:

1. A method for improving the production of small molecules in submerged *Corynebacterium* culture comprising adding to a submerged *Corynebacterium* culture a non-enzymatic fraction of spent formulated *Trichoderma* fermentation broth, wherein the *Corynebacterium* grown in the presence of the non-enzymatic fraction of spent formulated *Trichoderma* fermentation broth produce an increased amount of small molecules compared to *Corynebacterium* grown in an otherwise identical submerged culture in the absence of the non-enzymatic fraction of spent formulated *Trichoderma* fermentation broth, wherein the increase in small molecule production is not due to enzymatic activity in the spent formulated *Trichoderma* fermentation broth, and
wherein the small molecule is an amino acid selected from glutamic acid and lysine
and wherein the spent formulated *Trichoderma* fermentation broth is produced by filtering whole or fractionated spent *Trichoderma* fermentation broth and comprises between 33-45% w/w water, between 47-53% w/w glycerol and between 3-4% w/w sodium chloride, and a pH of 4.5-5.0.

2. The method of claim 1, wherein the non-enzymatic fraction of spent formulated *Trichoderma* fermentation broth is produced by heat treating whole or fractionated spent formulated *Trichoderma* fermentation broth.

3. The method of claim 1, wherein the non-enzymatic fraction of spent formulated *Trichoderma* fermentation broth used to increase small molecule production is a component of whole or fractionated spent *Trichoderma* fermentation broth that is added to the submerged *Corynebacterium* culture.

4. The method of claim 1, wherein at least a portion of the total dose of the spent formulated fermentation broth is initially added to the *Corynebacterium* culture.

5. The method of claim 1, wherein the spent formulated fermentation broth is harvested from a *Trichoderma* growth culture at least 29 hours following inoculation of *Trichoderma* broth.

6. The method of claim 1, wherein the spent formulated fermentation broth is harvested from a *Trichoderma* growth culture prior to expression of a protein of interest in the broth.

7. The method of claim 1, wherein the increase in small molecule production is not the result of increased cell mass in the *Corynebacterium* culture.

\* \* \* \* \*